United States Patent
Sakai

(10) Patent No.: US 6,683,685 B2
(45) Date of Patent: Jan. 27, 2004

(54) ATOMIC ABSORPTION PHOTOMETER

(75) Inventor: Masumi Sakai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 273 days.

(21) Appl. No.: 10/000,097

(22) Filed: Dec. 4, 2001

(65) Prior Publication Data

US 2002/0080351 A1 Jun. 27, 2002

(30) Foreign Application Priority Data

Dec. 25, 2000 (JP) .......................................... 2000-392077

(51) Int. Cl.[7] .................................................. G01J 3/36
(52) U.S. Cl. ........................................ 356/307; 356/309
(58) Field of Search .................................. 356/307, 312, 356/311, 315, 316, 319, 328, 308, 309

(56) References Cited

U.S. PATENT DOCUMENTS

| 4,462,685 A | * | 7/1984 | Smith et al. | 356/307 |
|---|---|---|---|---|
| 4,948,250 A | * | 8/1990 | Oishi et al. | 356/307 |
| 5,042,946 A | * | 8/1991 | Harada | 356/307 |
| 5,104,220 A | * | 4/1992 | Okumoto et al. | 356/307 |
| 5,181,077 A | * | 1/1993 | Dencks et al. | 356/307 |
| 5,568,254 A | * | 10/1996 | Nakano | 356/307 |

* cited by examiner

Primary Examiner—Frank G. Font
Assistant Examiner—Layla Lauchman
(74) Attorney, Agent, or Firm—Kanesaka & Takeuchi

(57) ABSTRACT

In an atomic absorption photometer, depending on a fact whether a background correction is carried out or not, a pattern of a pulse lighting of light sources and a timing of sampling a light receiving signal are changed. Namely, at the time of a background correction measurement, one cycle is divided into three periods, that is, a period of lighting HCL, a period of lighting D2L, and an off period, and at the time of a measurement without a background correction, one cycle is divided into the period of lighting HCL and the off period. Accordingly, at the time of the measurement without the background correction, the period of lighting HCL and the off period become longer, and signal-to-noise ratio of the light receiving signal is improved. Accordingly, an absorbance with high accuracy can be calculated.

6 Claims, 5 Drawing Sheets

ATOMIC ABSORPTION PHOTOMETER

BACKGROUND OF THE INVENTION AND RELATED ART STATEMENT

The present invention relates to an atomic absorption photometer, and more particularly, to an atomic absorption photometer which carries out a correction in a background absorption using a continuous spectrum source, such as a deuterium lamp.

When atomic absorption photometers are roughly classified, there are a flame method and a furnace method. In the flame method, a sample is sprayed in a flammable gas, and by burning the mixed gas on a burner head, the sample is heated at a high temperature to be atomized. Then, a measuring beam is allowed to pass through the atomic vapor to thereby measure an absorbance. In the furnace method, a sample is held in a graphite tube (heating tube), and by heating the tube, the sample is heated at a high temperature to be atomized. Then, the measuring beam is allowed to pass through the atomic vapor to thereby measure the absorbance.

In these atomic absorption analyses, for example, in case a large amount of salts and the like are mixed in the sample, they are not completely dissociated even at the high temperature, and may cause the scattering and absorption with respect to the measuring beam from a light source. Also, in the flame method, if a flame temperature is low, an absorption by a molecular type in the flame may occur. These phenomena are called a background absorption. In case of using a light source which emits a bright line spectrum, such as a hollow cathode lamp (HCL) which is often used as the light source in general, an absorbance by the atomic absorption of the specified element is added to an absorbance by the background absorption described above. Thus, it is difficult to obtain the accurate absorbance.

Therefore, there has been conventionally conducted a correction called a deuterium lamp background correction, which is also called a continuous spectrum source system. Namely, other than the light source which emits the bright line spectrum, an absorbance with respect to a measuring beam from a light source which emits a continuous spectrum (normally, the deuterium lamp is used) is measured at the same time. In case of using the light source which emits the continuous spectrum, since a wavelength bandwidth is extremely broad, the absorbance due to the atomic absorption of the specified element is small such that it can be substantially ignored, and it can be considered that only the absorbance by the background absorption is measured. Therefore, by calculating a difference between these absorbances, an effect by the background absorption is eliminated, and only the absorbance by the specified element can be obtained. Incidentally, throughout the specification of the present invention, in case the background correction is merely referred to, it means the background correction using the deuterium lamp.

Also, as an error factor other than the background absorption, there might be an effect of an extraneous light or outside light. Namely, the flame in the flame method and the graphite tube in the furnace method emit lights by themselves, and since a sample chamber becomes hot in the atomic absorption photometer, the sample chamber is often in an open condition, so that the light from outside may be introduced into a spectroscope. Although these lights are irrelevant to the atomic absorption, in case these lights have components of wavelengths which are observed, they cause enormous errors in the measurement. Thus, it is necessary to eliminate these lights.

In order to eliminate the effect of the background correction and the outside light, in the conventional atomic absorption photometer, lights or pulse lights of the light sources are controlled so that three periods, that is, a period of light of only the hollow cathode lamp, a period of light of only the deuterium lamp, and an off period of tuning of f both lamps, are provided. Then, during the off period, a signal $z$ due to the outside light or dark current of a photodetector itself is obtained, and by subtracting the signal $z$ respectively from a light receiving signal $h$ obtained at the photodetector during the period of light of only the hollow cathode lamp, and from a light receiving signal $d$ obtained at the photodetector during the period of light of only the deuterium lamp, light receiving signals h' and d', in which the effect of the outside light is eliminated, are obtained. Furthermore, absorbances are respectively calculated from the light receiving signals h' and d', and by finding the difference between these absorbances, the background correction is carried out.

In the atomic absorption analysis, the background correction is not always carried out, and for example, in case it is known in advance that the sample does not contain substances which cause the background absorption, the background correction is not required. Also, in case a measurement object wavelength is in a wavelength region (more than 425 nm) in which an emission spectrum of the deuterium lamp is very weak, the background correction is not useful, so that it is not required. At the time of the measurement without the background correction described above, in the conventional atomic absorption photometer, there is carried out only a control such that the deuterium lamp which is unnecessary as the measuring beam is left to be turned off, and it has not been considered to positively improve a signal-to-noise ratio of the signal at the time of measurement without the background correction.

Accordingly, the present invention has been made in view of the foregoing, and an object of the invention is to provide an atomic absorption photometer, in which a signal-to-noise ratio of a light receiving signal at the time of measurement without background correction is improved, so that the absorbance can be calculated with high accuracy.

Further objects and advantages of the invention will be apparent from the following description of the invention.

SUMMARY OF THE INVENTION

To achieve the aforementioned object, the present invention provides an atomic absorption photometer, in which light emitted from a light source is allowed to pass through an atomization section, and the light passing through the atomization section is introduced into a photodetector or first photodetector to measure an intensity thereof, so that an absorbance at the atomization section is calculated from a signal from the photodetector. The atomic absorption photometer as stated above comprises a first light source for emitting a bright line spectrum light; a second light source for emitting a continuous spectrum light; and measurement controlling means for dividing a predetermined measurement period into three periods formed of a first measurement period by a light emitted from the first light source, a second measurement period by a light emitted from the second light source, and a third measurement period in a condition that neither of emitted lights from the first and second light sources are emitted on the photodetector in case a background correction is carried out. Also, the measurement controlling means distributes the second measurement period to one or both of the first measurement period and the third measurement period in case the background correction is not carried out.

At the time of the measurement without the background correction, the measurement by the light emitted from the second light (for example, deuterium lamp) is not required. Thus, in this case, the measurement controlling means distributes the second measurement period, which is assigned to the measurement by the emitted light from the second light source in case of the measurement with the background correction, to one or both of the first measurement period by the emitted light from the first light source and the third measurement period in the condition that neither of the emitted lights from both the light sources are emitted. Therefore, at least one of the first measurement period and the third measurement period becomes longer than that at the time of the measurement with the background correction.

In the photodetector which receives the measuring beam or light, as a period of time for receiving the measuring beam becomes longer, the light receiving signals are integrated to thereby improve the signal-to-noise ratio. If the signal-to-noise ratio of the light receiving signal is improved, the accuracy of the absorbance calculated based on the light receiving signal is improved. Thus, according to the atomic absorption photometer of the invention, especially in case the measurement without the background correction is carried out, the signal-to-noise ratio of the light receiving signal is improved as compared with the conventional atomic absorption photometer, resulting in increasing the accuracy of the absorbance.

Also, in the atomic absorption photometer according to the present invention, there may be provided filtering means for reducing a radio-frequency region of the light receiving signal by the photodetector, and the cut-off frequency of the filtering means can be changed in accordance with the existence of the background correction.

The filtering means is provided for removing a high frequency noise contained in the light receiving signal, and it is preferable to set a high region cut-off frequency of the filtering means as low as possible within a range of not losing the frequency component as the object. Normally, since the cut-off frequency is determined by the repeating cycle of the first measurement period, the second measurement period, and the third measurement period, in case the second measurement period is distributed to the first and third measurement periods as described above, the cut-off frequency can be lowered. According to this structure, since the high frequency noise is further reduced in case the background correction is not carried out, the signal-to-noise ratio of the light receiving signal can be further improved.

Also, the atomic absorption photometer according to the present invention may be further provided with a second photodetector including a detection sensitivity in a long wavelength region, and an optical path switching means for selectively introducing the light passing through the atomization section into one of the photodetector and the second photodetector. In this structure, in case the background correction is not carried out, the optical path switching means switches the optical path such that the light is introduced into the second photodetector.

Here, for example, the first photodetector is a photomultiplier, and the second photodetector is a photodiode. Although the photodiode has a disadvantage in the response speed, in case the second measurement period is distributed to the first and third measurement periods as described above, the first and third measurement periods become longer, and the slowness of the response speed does not cause so much problem. In general, since the background correction is not carried out in most of the cases when the wavelength as the measurement object is in a long wavelength region outside a range of the wavelengths of the emitted light of the deuterium lamp, it is possible to sufficiently use the detector, such as photodiode, which does not have a detection sensitivity in a short wavelength region. According to this structure, since the detection of the light in the long wavelength region can be assigned to the second photodetector, the photodetector having the detection sensitivity in the short wavelength region is sufficient. Among the photomultipliers, the photomultiplier having this characteristic is considerably cheaper than a photomultiplier having a high detection sensitivity also in the long wavelength region, and the photodiode is much cheaper. Therefore, according to this structure, the cost of the atomic absorption photometer can be further reduced.

DETAILED DESCRIPTION OF PREFERRED EMBODIMENTS

Hereunder, an atomic absorption photometer as a first embodiment of the invention will be explained with reference to the accompanied drawings. In this example, the present invention is applied to a furnace type atomic absorption photometer. However, as clearly understood from the explanation described later, since a difference in the atomization section is not relevant to the present invention, it is needless to say that the present invention can be applied to the flame type atomic absorption photometer.

Figure 1:
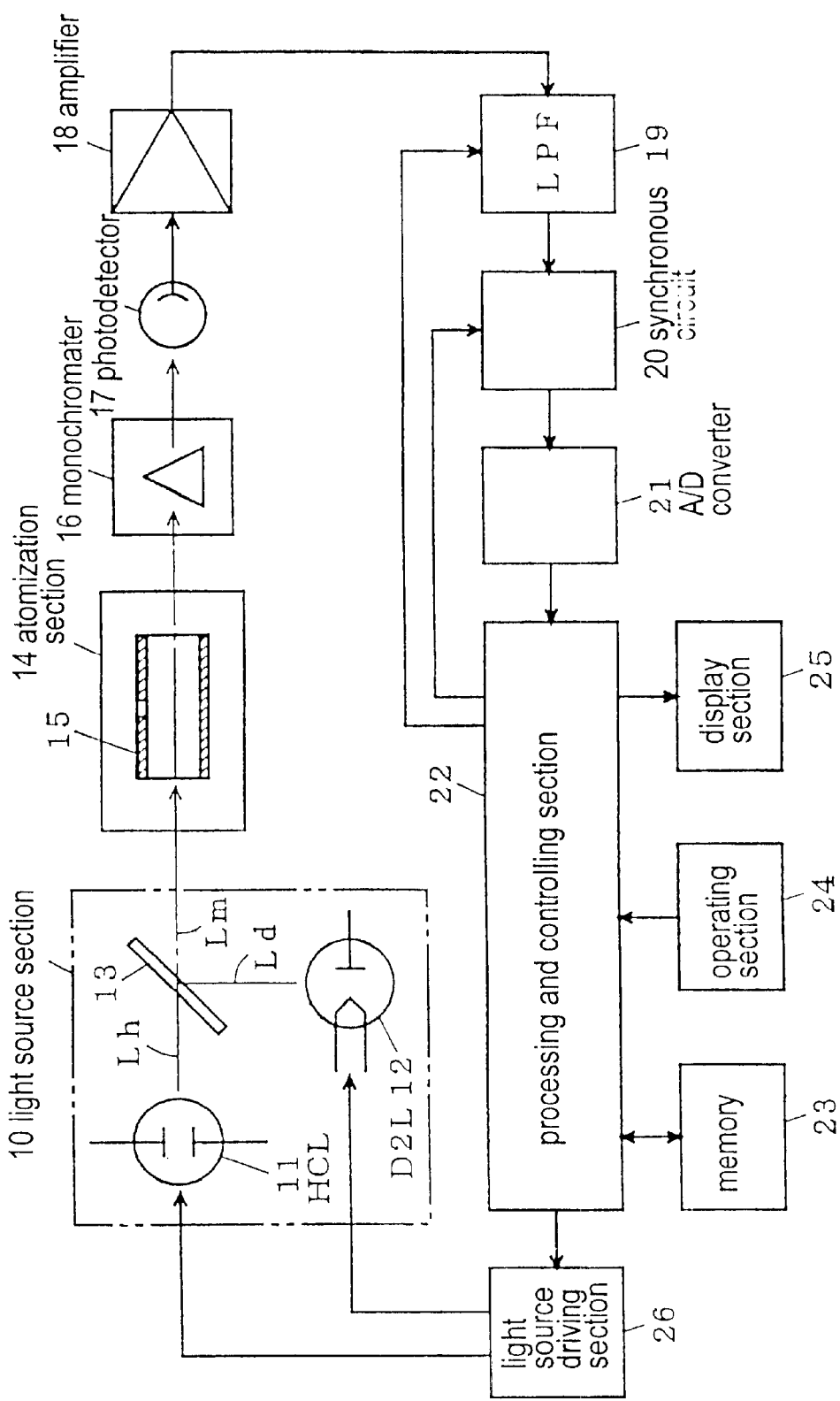
FIG. 1 is a block diagram showing a structure of a main section of an atomic absorption photometer according to a first embodiment of the invention.

FIG. 1 is a block diagram showing a structure of a main section of the atomic absorption photometer of the first embodiment. A light source section 10 includes a hollow cathode lamp (HCL) 11, a deuterium lamp (D2L) 12, and a half mirror 13. A light or beam including a bright line spectrum emitted from the HCL 11 becomes HCL luminous flux Lh, and HCL luminous flux Lh is received on the half mirror 13. On the other hand, a light or beam emitted from the D2L 12 becomes D2L luminous flux Ld, which is received on the half mirror. At the half mirror 13, the HCL luminous flux Lh and D2L luminous flux Ld are combined into a single luminous flux Lm. However, the HCL 11 and D2L 12 are controlled to be subjected to pulse light by a light source driving section 26 under a control by a processing and controlling section 22, described later, and the luminous flux Lm results from a time division multiplexing of the HCL luminous flux Lh and D2L luminous flux Ld including off time. The luminous flux Lm passes through an inside of a graphite tube 15 of an atomization section 14 to be introduced into a monochromator 16, and light with a predetermined wavelength is taken out by the monochromator 16 and sent to a photodetector 17.

Incidentally, although not shown in the drawing, adequate condensing optical systems are provided respectively between the light source section 10 and the atomization section 14, and between the atomization section 14 and the monochromator 16, and these condensing optical systems condense the luminous fluxes adequately to thereby introduce the condensed luminous flux to the next stage.

Electric signal obtained by being photoelectrically converted at the photodetector 17 are amplified at an amplifier 18, and a radio-frequency noise is removed at a low pass filter (LPF) 19. Then, the electric signals are separated into the respective signals corresponding to light of the HCL, light of the D2L, and off condition of both lamps at a synchronous circuit 20, and are further converted into digital signals at an analog-to-digital converter 21 to be inputted into the processing and controlling section 22. The processing and controlling section 22 is mainly formed of a computer including a CPU, and the processing and controlling section 22 carries out various operation processes and outputs control signals for controlling operations of the respective sections described above. Also, the processing and controlling section 22 is connected to a memory 23, an operating section 24, such as a keyboard, and a display section 25, such as CRT (cathode ray tube) display.

At the time of a quantitative analysis of the sample, a large current is allowed to flow from a current source, not shown, through the graphite tube 15, so that the graphite tube 15 is heated. Then, a sample liquid is introduced into the graphite tube 15 from a sample injection port provided at an upper section of the graphite tube 15, and the sample is atomized therein. As described above, in the light passing through the graphite tube 15, the light having the wavelength peculiar to the element contained in the sample is intensely absorbed. The processing and controlling section 22 calculates a ratio between a light receiving intensity without being subjected to the absorption and a light receiving intensity subjected to the absorption, and the sample is quantified from the absorbance obtained as described above.

Figure 2:
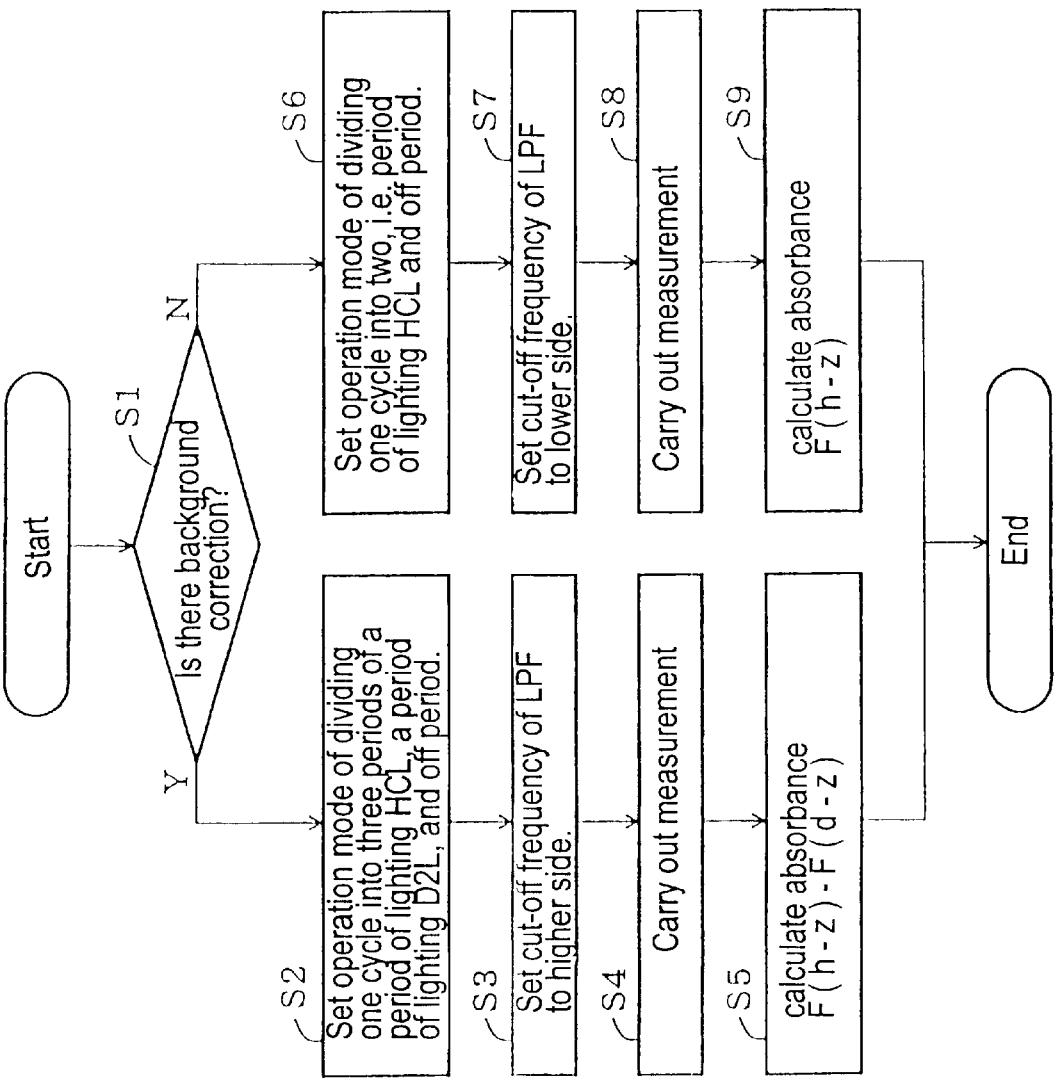
FIG. 2 is a flow chart showing characteristic operations in the atomic absorption photometer of the first embodiment of the invention.

Next, characteristic processing operations in the atomic absorption photometer according to the first embodiment will be explained in accordance with a flow chart shown in FIG. 2. Also, FIGS. 3(a) to 3(d) are timing charts for explaining the processing operations.

When an operator sets various parameters from the operating section 24 prior to the measurement, as one of the parameters, the operator selects whether the background correction is required or not. When the measurement is started, the processing and controlling section 22 determines whether a background correction is required or not (step S1). In case of the background correction measurement, processes in steps S2 through S5 are sequentially carried out, and in case of the measurement without the background correction, processes in steps S6 through S9 are sequentially carried out.

Figure 3:
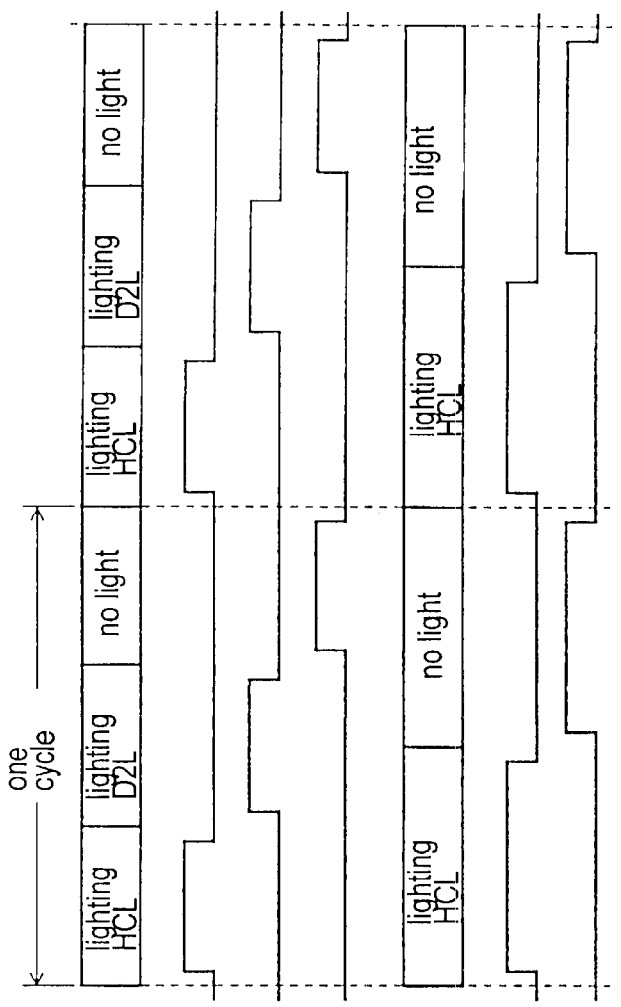
FIGS. 3(a) to 3(d) are timing charts for explaining the operations of the atomic absorption photometer.

Namely, in case of the background correction measurement, there is set an operation mode such that a measurement period of one cycle is divided into three periods, that is, a period of lighting HCL, a period of lighting D2L, and an off period of tuning off both light sources (step S2), and furthermore, it is set to switch a cut-off frequency of the LPF 19 to a higher side (step S3). Then, by operating the light source driving section 26 and the synchronous circuit 20 in accordance with the operation mode described above, the measurement is carried out (step S4). At this time, the respective operation conditions become as shown in FIG. 3(a), and for example, the D2L 12 is turned off during the period of lighting HCL, and the light receiving signal obtained at the photodetector 17 at this moment is sampled during a period of pulse signal "1" shown at (b1) in FIG. 3(b), to thereby utilize the same as the light receiving signal with respect to the emitted light from the HCL 11. The same operations are carried out in the period of lighting D2L and the off period.

Therefore, from the measurement described above, there can be obtained the light receiving signal $\underline{h}$ with respect to the emitted light from the HCL 11, a light receiving signal $\underline{d}$ with respect to the emitted light from the D2L 12, a light receiving signal $\underline{z}$ (due to the outside light, dark current or the like) with respect to the off period, so that the absorbance after conducting the background correction and the elimination of the outside light is calculated from the following formula (step S5).

$$\text{Absorbance} = F(h-z) - F(d-z)$$

Here, F(x) is a formula for calculating the absorbance with respect to a light receiving signal $\underline{x}$.

On the other hand, in case of the measurement without the background correction, there is set an operation mode such that the same measurement period of one cycle is divided into two periods, that is, the period of lighting HCL and the off period (step S6), and furthermore, it is set to switch the cut-off frequency of the LPF 19 to a lower side (step S7). Then, the light source driving section 26 and the synchronous circuit 20 are operated to carry out the measurement (step S8). The respective operation conditions are shown in FIG. 3(c), and at this time, the period of lighting D2L which is necessary for the background correction is not provided, and for that portion, the period of lighting HCL and the off period become relatively longer. In this example, one cycle is substantially equally divided into three at the time of the background correction measurement, and one cycle is substantially equally divided into two at the time of the measurement without the background correction. Therefore, the period of lighting HCL and the off period at the time of the measurement without background correction are respectively about one and a half times longer than those at the time of the background correction measurement. Therefore, for those longer periods, electrons are integrated at the photodetector 17, so that the signal-to-noise ratio of the light receiving signal is improved.

Also, since it is necessary that the LPF 19 allows signal change components, which correspond to alternation cycles of the respective periods within the period of one cycle described above, to pass therethrough, in the measurement without background correction in which the alternation cycle is relatively slow, the cut-off frequency of the LPF 19 can be lowered. Therefore, the high frequency noise contained in the signal is reduced accordingly, and in view of this aspect, the present invention is effective for improving the signal-to-noise ratio of the received signal. Incidentally, for example, in the LPF by an RC circuit, switching the cut-off frequency can be carried out by a structure of changing a value of R or C by a switch.

From the measurement described above, there can be obtained the light receiving signal $\underline{h}$ with respect to the emitted light from the HCL 11, and the light receiving signal $\underline{z}$ (due to the dark current or the like) with respect to the off period. Thus, the absorbance after conducting the elimination of the outside light is calculated by the following formula (step S9).

$$\text{Absorbance} = F(h-z)$$

Since the signal-to-noise ratios of the light receiving signals $\underline{h}$ and $\underline{z}$ are higher than those in the conventional atomic absorption photometer, the accuracy of the absorbance is improved consequently.

Incidentally, instead of lighting and turning off the HCL 11 and D2L 12, it can be structured that a rotating sector mirror is used to selectively introduce lights into the atomization section, and at the same time, by utilizing a rotating chopper, the light to be provided on the photodetector 17 may be intercepted to produce a period corresponding to the off period.

Also, although the measurement period of one cycle is divided equally into two or three in the aforementioned embodiment, it is not always necessary to divide the period equally.

Further, although the aforementioned embodiment has the structure of the single beam system, the present invention can be applied to a structure of a dual beam system. In this case, the pulse signal which controls on/off turning of the light source is synchronized with an operation of a mechanism of splitting the luminous flux, such as a chopper mirror, and it may be controlled that the light source is not lighted up during a period corresponding to a boundary of splitting the luminous flux.

Figure 4:
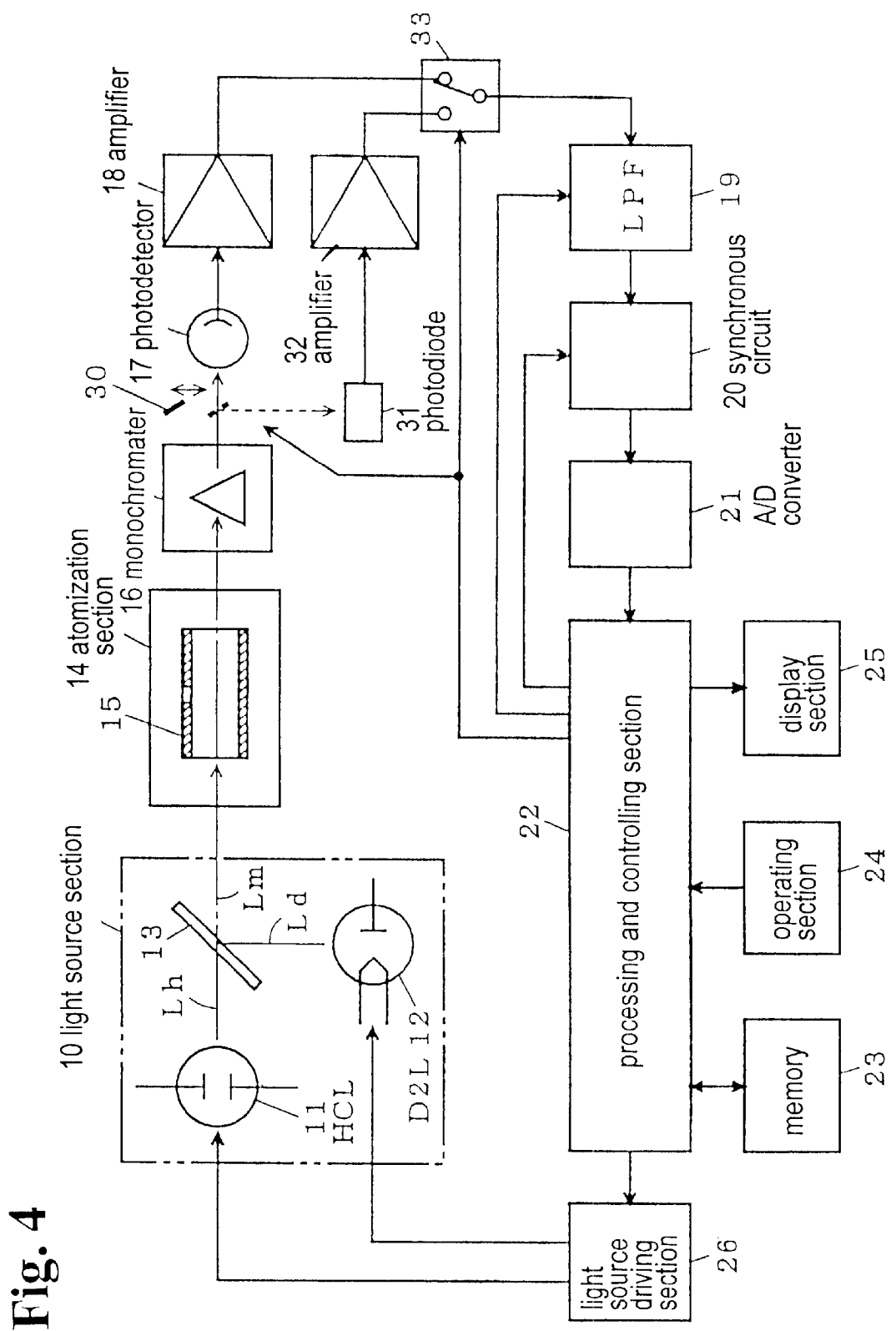
FIG. 4 is a block diagram showing a structure of a main section of an atomic absorption photometer according to a second embodiment of the invention.

Next, an atomic absorption photometer according to a second embodiment of the invention will be explained with reference to FIG. 4 and FIG. 5. FIG. 4 is a block diagram showing an entire structure of the atomic absorption photometer according to the second embodiment, and FIG. 5 is a graph schematically showing the detection sensitivity characteristics of the elements used as photodetectors in the atomic absorption photometer of the second embodiment.

Figure 5:
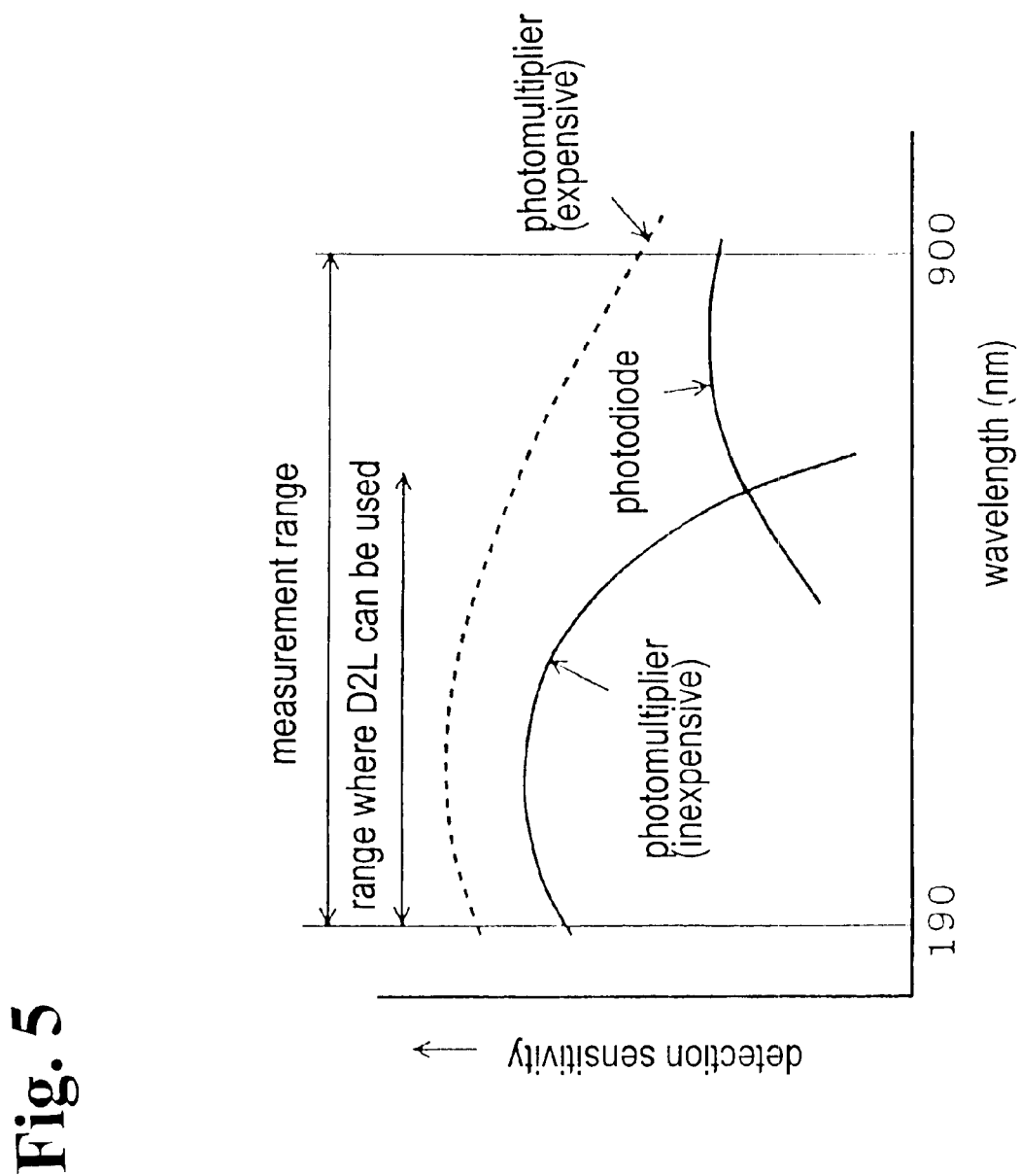
FIG. 5 is a graph schematically showing detection sensitivity characteristics of elements used as a photodetector in the atomic absorption photometer according to the second embodiment of the invention.

In case a wide range in the order of 190 to 900 nm is required to be covered as a measurement wavelength region in the atomic absorption analysis, in order to correspond to this wide range by using a single photodetector as in the first embodiment, it is necessary to use a photomultiplier having a characteristic shown by a broken line in FIG. 5. In general, this kind of photomultiplier is considerably expensive. On the contrary, in a relatively inexpensive photomultiplier, although enough detection sensitivities can be obtained in a short wavelength region, since the detection sensitivity is drastically lowered in the long wavelength region (more than 650 nm), it is difficult to cover the entire wavelength region. On the other hand, there is a photodiode as a further inexpensive detector, and even though the photodiode is inferior to a high performance photomultiplier in the long wavelength region in the order of 400 to 1000 nm, the photodiode has enough detection sensitivities in the long wavelength region. However, in the photodiode, if it is tried to increase gains especially, the response speed of the photodiode becomes slower, so that it can not follow the high speed on/off cycle.

In the atomic absorption photometer of the second embodiment, by utilizing that the period of lighting the HCL 11 becomes substantially longer at the time of the measurement without the background correction as described above, the inexpensive photomultiplier and the photodiode can be adopted as the photodetector. Namely, in FIG. 4, the photodetector 17 is, for example, a photomultiplier which is inexpensive and has high detection sensitivities only in the short wavelength region as shown by a solid line in FIG. 5.

Before the photodetector 17, there is provided a mirror 30 for switching the optical path, which is capable of being freely inserted into the optical path and retreated therefrom, and in case the mirror 30 is inserted into the optical path, the light taken out at the spectroscope 16 is introduced into a photodiode 31. Also, an electric signal obtained by being photoelectrically converted by the photodiode 31 is amplified at an amplifier 32, and selected as an output of the amplifier 18 by a turnover switch 33 to be inputted into the LPF 19.

In this atomic absorption photometer, in case the background correction measurement is carried out, the processing and controlling section 22 allows the mirror 30 to be retreated from the optical path, and by bringing the turnover switch 33 to the right in the figure, the processing and controlling section 22 allows the output of the amplifier 18 to be inputted into the LPF 19. Accordingly, the operations explained in the first embodiment are achieved. On the other hand, at the time of the measurement without the background correction, the mirror 30 is inserted into the optical path, and by bringing the turnover switch 33 to the left, the output of the amplifier 32 is inputted into the LPF 19. Accordingly, the measuring beam which has passed through the inside of the graphite tube 15 is introduced onto the photodiode 31, and the light receiving signal thereof is sent to the LPF 19 via the amplifier 32.

In general, the measurement without the background correction is selected mostly when the measurement object wavelength is a long wavelength region where an emission spectrum of the D2L 12 is extremely weak (wavelength region more than 425 nm) so that the background correction is substantially meaningless. Therefore, there is no problem even if the photodiode 31, which has almost no detection sensitivity in the short wavelength region, is used as the detector at the time of the measurement without the background correction. Needless to say, since the measurement in the short wavelength region is expected at the time of the background correction measurement, there is no problem of using the inexpensive photomultiplier which has almost no detection sensitivity in the long wavelength region.

As described above, in the atomic absorption photometer of the second embodiment, in accordance with the selection between the background correction measurement and the measurement without the background correction, the photomultiplier and the photodiode can be properly and alternately used as the photodetector. As described above, the corresponding wavelength regions of the respective elements can be limited, respectively, and even if costs of these two elements, the mirror 30 and other additional parts are added, the cost of the atomic absorption photometer of the invention can be lower than that of the atomic absorption photometer in which a single, expensive and high-performance photomultiplier is used.

Incidentally, the aforementioned embodiments are examples of the invention, and can be adequately modified within the gist of the present invention.

What is claimed is:

1. An atomic absorption photometer, comprising:
   a light source formed of a first light source for emitting a bright line spectrum light and a second light source for emitting a continuous spectrum light,
   an atomization section for allowing a light emitted from the light source to pass therethrough to measure a material thereat,
   a first photodetector for receiving the light passing through the atomization section, said first photodetector measuring an intensity of the light to issue a signal thereof so that an absorbance at the atomization section is calculated, and measurement controlling means for controlling the light source and the first photodetector, said controlling means, in case a background correction is carried out, dividing a predetermined measurement period into three periods formed of a first measurement period measured by a light emitted from the first light source, a second measurement period measured by a light emitted from the second light source, and a third measurement period measured in a condition that no lights from the first and second light sources are emitted on the photodetector, said measurement controlling means distributing the second measurement period to at least one of the first measurement period and the third measurement period in case the background correction is not carried out.

2. An atomic absorption photometer according to claim 1, further comprising filtering means electrically connected to the photodetector and the controlling means for reducing a radio-frequency region of a light receiving signal by the first photodetector, said filtering means having a cut-off frequency varied in accordance with an existence of the background correction.

3. An atomic absorption photometer according to claim 1, further comprising a second photodetector having a detection sensitivity in a wavelength region different from that of the first photodetector, and optical path switching means for selectively introducing the light passing through the atomization section into one of the first photodetector and the second photodetector, said optical path switching means switching an optical path such that the light is introduced into the second photodetector in case the background correction is not carried out.

4. An atomic absorption photometer according to claim 3, wherein said second photodetector has the detection sensitivity in a wavelength region between about 400 and 1000 nm.

5. An atomic absorption photometer according to claim 1, further comprising a spectroscope situated between the first photodetector and the atomization section.

6. An atomic absorption photometer according to claim 1, wherein said light source further includes means to combine the bright line spectrum light from the first light source and the continuous spectrum light from second light source, said means introducing the lights to the atomization section.

* * * * *